United States Patent [19]

Duvieilh

[11] Patent Number: 4,911,725
[45] Date of Patent: Mar. 27, 1990

[54] GOLFING ATTACHMENT FOR PROSTHESIS

[75] Inventor: Milton L. Duvieilh, Metairie, La.

[73] Assignee: Mil-Glo Corporation, Metairie, La.

[21] Appl. No.: 558,045

[22] Filed: Dec. 5, 1983

[51] Int. Cl.⁴ .................................................. A61F 2/54
[52] U.S. Cl. ......................................................... 623/65
[58] Field of Search ................... 403/223; 3/12.4, 12.8; 269/287; 273/80.1, 80.2

[56] References Cited

U.S. PATENT DOCUMENTS

| | | | |
|---|---|---|---|
| 826,102 | 7/1906 | Hersey | 403/223 |
| 1,985,427 | 12/1934 | Richardson | 403/223 |
| 2,561,523 | 7/1951 | Lux . | |
| 2,566,512 | 8/1951 | Croix . | |
| 2,931,661 | 4/1960 | Harris | 403/223 |
| 3,434,163 | 3/1969 | Saverino | 3/12.8 |
| 3,747,128 | 7/1973 | DiFilipo | 3/12.8 |
| 3,965,491 | 6/1976 | Frenzel . | |
| 4,357,717 | 11/1982 | Puhl | 3/12.8 |

FOREIGN PATENT DOCUMENTS

| | | | |
|---|---|---|---|
| 306713 | 7/1918 | Fed. Rep. of Germany | 3/12.8 |
| 515425 | 11/1920 | France | 3/12.8 |

*Primary Examiner*—Richard J. Apley
*Assistant Examiner*—David J. Isabella
*Attorney, Agent, or Firm*—Roylance, Abrams, Berdo & Goodman

[57] ABSTRACT

A golfing attachment for connecting a golf club to a prosthesis comprises a base portion, a coupling attached to and extending from one end of the base portion for connection to a prosthesis, and a flexible and resilient plastic tube. The tube extends axially from the opposite end of the base portion and coaxially relative to the coupling. A golf club has a handle portion inserted into and secured to the tube such that the tube forms a flexible connection between the prosthesis and the golf club.

15 Claims, 1 Drawing Sheet

GOLFING ATTACHMENT FOR PROSTHESIS

BACKGROUND OF THE INVENTION

1. Field of the Invention

The present invention relates to an attachment for connecting an implement to a prosthetic arm. More particularly, the present invention relates to an attachment which provides a flexible and resilient connection between a prosthetic arm and a golf club.

2. Description of the Prior Art

Conventional prosthetic attachments for connecting a sports implement to a prosthetic arm are complicated, expensive, and difficult to operate. Additionally, they do not provide adequate flexibility and do not simulate the usual wrist motion critical to proper swinging of the implement. Further, the conventional devices orient the implement at an angle to and/or laterally offset from the longitudinal axis of the prosthesis, thereby connecting the implement to the arm in an abnormal manner and making manipulation of the implement more difficult.

One conventional device comprises a rigid U-shaped solid plastic member with a coupling for attaching the device to a prosthetic arm on the end of one leg, and a semi-cylindrical golf club fitting on the other, parallel leg. The shaft of the club is held in the semi-cylindrical metal fitting by a locking device and by the other hand of the golfer. However, this device laterally offsets the club relative to the prosthetic arm in an unnatural manner and does not have sufficient resiliency and flexibility to simulate wrist motion.

Another device is disclosed in U.S. Pat. No. 4,357,717 to Puhl. The Puhl device is relatively complex and orients the club at an acute angle relative to the prosthetic arm. Although the Puhl device includes a flexible bar, such bar has metal support bars extending through the entire length thereof for securing a separate clamp for engaging the golf club.

Other relatively complex devices for attaching golf clubs are disclosed in U.S. Pat. No. 3,965,491 to Frenzel and U.S. Pat. No. 3,747,128 to De Filipo. However, such devices do not provide resilient and flexible connections which will simulate normal wrist motion.

SUMMARY OF THE INVENTION

An object of the present invention is to provide an attachment for connecting an implement to a prosthesis which is easy to operate and simulates normal wrist motion.

Another object of the present invention is to provide an attachment for connecting an implement to a prosthesis which is of rugged construction, and is simple and inexpensive to manufacture.

A further object of the present invention is to provide a golfing attachment for connecting a golf club to a prosthesis which will permit the golfer to hold and swing the club in a relatively normal manner.

A still further object of the present invention is to provide an attachment for connecting an implement to a prosthesis which can be readily mounted to the prosthesis and to the implement, and which can be easily repaired.

The foregoing objects are obtained by an attachment for a prosthesis comprising a base portion having opposite ends, a coupling attached to and extending from one end of the base portion and a flexible and resilient plastic tube. The coupling releasably attaches the base portion to a prosthesis. The tube extends axially from the other end of the base portion and coaxially relative to the coupling, and is attached to the base portion. In this manner, an implement can be releasably coupled to the prosthesis by inserting and securing one end of the implement within the tube.

The foregoing objects are also obtained by a golfing attachment for connecting a golf club to a prosthesis comprising a base portion having opposite ends, a coupling attached to and extending from one end of the base portion for releasably attaching the base portion to a prosthesis, and a flexible and resilient tube. The tube extends axially from the other end of the base portion and is attached to the base portion. A golf club having a handle portion is inserted into and secured to the tube such that the tube forms a flexible connection between the prosthesis and the golf club.

By performing the prosthetic attachment in this manner, the resilient and flexible tube orients the implement coaxially relative to the arm and provides a resilient and flexible connection simulating normal wrist motion. Thus, the implement can be held in a relatively normal manner. For golf clubs, this permits the golfer to use a substantially normal golf swing.

The simple construction of the attachment permits it to be operated and manufactured simply and inexpensively. Additionally, such attachment is rugged and has a relatively long use life.

By attaching the tube in a releasable manner to the base portion, the attachment can be readily repaired by replacing the tube.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure.

DETAILED DESCRIPTION OF THE PREFERRED EMBODIMENT OF THE INVENTION

Figure 1:
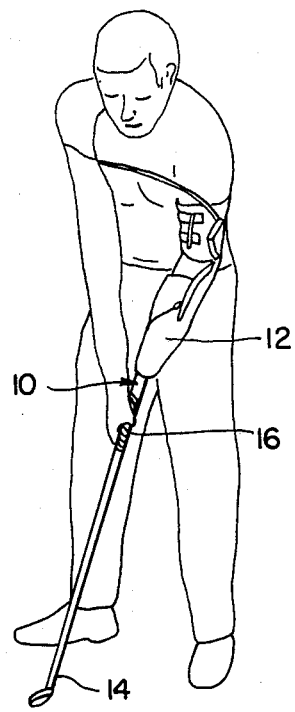
FIG. 1 is a perspective view of a golfer using an attachment according to the present invention.

Referring initially to FIG. 1, an attachment 10 according to the present invention is connected to the prosthetic arm 12 of a golfer for use with a golf club 14. The club can be secured within the attachment by tape 16.

Figure 2:
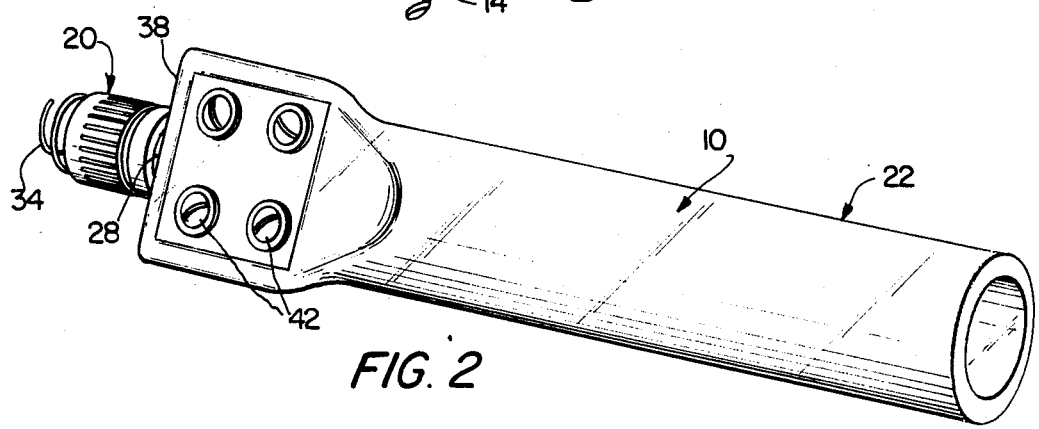
FIG. 2 is a perspective view of an attachment according to the present invention without an implement.
Figure 3:
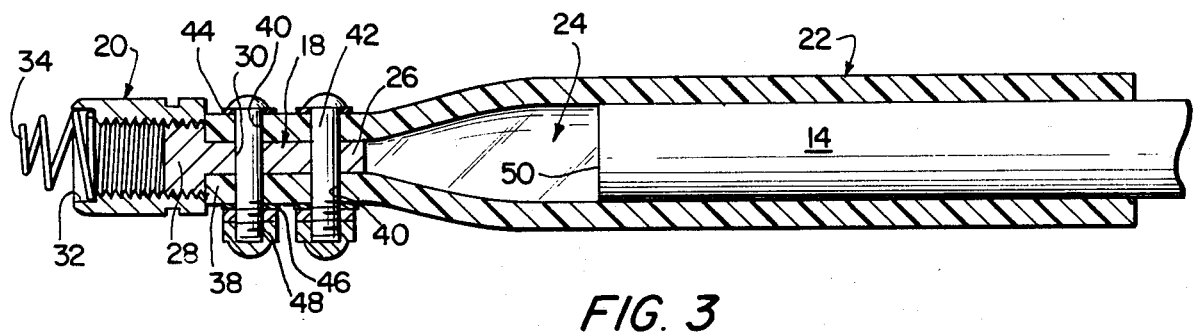
FIG. 3 is a side elevational view in section of the attachment of FIG. 2 with an implement inserted therein.

The details of the attachment are illustrated in FIGS. 2 and 3. Attachment 10 comprises a base portion 18, a coupling 20 and a flexible and resilient plastic tube 22. Coupling 20 releasably attaches the base portion and tube to prosthetic arm 12. Tube 22 receives the handle of implement 14 which is inserted and secured within the hollow interior 24 of the tube 22.

Base portion 18 comprises a generally rectangular or parallelipiped shaped plate 26 and an extension 28. The plate and extension are formed unitarily as a single piece. A plurality of bores 30 are formed in and extend entirely through plate 26. Four bores in a suitable arrangement re usually formed within the plate. Typically, plate 26 is about 1.25 inches by 1.25 inches, and is approximately 3/16 inch thick, and can be formed of stainless steel.

Extension 28 is generally cylindrical and is externally threaded. The size and threading of the extension conform to the corresponding dimensions of the internal bore of the standard prosthetic coupling.

Coupling 20 comprises an internally threaded sleeve having a recess 32 at one end housing an axially extending compression spring 34. The end of internally threaded bore of the coupling, opposite spring 34, receives externally threaded extension 28. A metal liquid can be employed to bond extension 38 to coupling 20 to secure these members together.

Plastic tube 22 is straight and can be of a commercial type normally used in connection with outboard motors and indoor plumbing. The main requirement is that the tube be of a material providing sufficient flexibility and resiliency to simulate normal wrist motion. The length of the tube is approximately six inches. The diameter of the tube is chosen to snugly receive the implement to be used therewith.

One end 38 of tube 22 is fitted over and surrounds plate 26. Plate 26 causes the tube adjacent end 38 to flatten. In the flattened portion of tube 22 adjacent end 38, aligned pairs of openings 40 are provided which are aligned with bores 30 in plate 26. The tube is secured to plate 26 by a plurality of bolts 42 extending through the respective aligned bores 30 and openings 40.

The head of each bolt overlies a washer 44 which in turn overlies an upper surface of the tube. Washers 46 and nuts 48 are mounted on the opposite ends of bolts 42 with the nuts threadedly engaging the external threads on the bolts to secure tube 22 to plate 26. In this manner, bolts 42 provide a detachable coupling between base portion 18 and tube 22 to permit replacement of tube 22.

An implement, such as a golf club 14, has its handle portion snugly received within hollow interior 24 of tube 22. Club 14 and tube 22 can be further secured together by adhesive tape wrapped about the tube and the golf club handle.

The upper end 50 of club 14 is spaced from plate 26 such that the portion of tube 22 between club end 50 and the adjacent end of plate 26 forms a flexible and resilient connection between prosthesis 12 and golf club 14. This flexible and resilient connection will permit movement simulating normal movement of a wrist, particularly in connection with the swinging of a golf club or other implement. Additionally, with the coaxial arrangement of coupling 20 and tube 22, golf club 14 will be oriented substantially coaxially with prosthesis 22. This coaxial arrangement corresponds to the normal or desired positioning between a golf club and arm during a proper swinging motion.

In use, a separate attachment 10 is mounted on each golf club by inserting a portion of the club shaft within the tube and securing the tube and shaft with tape. A chosen club may be used by the golfer by merely connecting coupling 20 to the prosthetic arm quickly and easily. Since the attachment of the present invention can be simply and inexpensively manufactured, an individual attachment for each club is economically feasible.

Preferably, coupling 20 is attached to prosthesis 12 such that attachment 10 is fixed axially, but can rotate freely about its longitudinal axis. This will permit the golfer to rotate the club during the swing. Conventional prosthetic couplings include releasable locking arrangements which permit attachments to be selectively coupled to a prosthesis in a relatively rotationally fixed or rotationally free manner.

The flexible and resilient plastic tube provides the flexibility and degree of movement required for full and smooth swings without the limitations or jerks experienced with conventional prosthetic attachments. The flexibility and positioning of the club by the plastic tube permits the golfer to swing in a natural manner without restrictions and with better results. The base portion of relatively rigid metal will not break. Additionally, the base portion can be easily and securely attached to the coupling.

The plastic tube can be simply and inexpensively replaced by the golfer. The useful life of the tube is approximately 2,000 hits. After such use, the tube will tend to tear.

While a particular embodiment has been chosen to illustrate the invention, it will be understood by those skilled in the art that various changes and modifications can be made therein without departing from the scope of the invention as defined in the appended claims.

What is claimed is:

1. An attachment for a prosthesis, comprising:
    a base portion having a plate with first and second opposite ends;
    coupling means, attached to and extending from said first end of said plate by an extension, for releasably attaching said base portion to a prosthesis;
    a flexible and resilient plastic tube extending axially from said second end and coaxially relative to said coupling means, said tube having a first end portion coupled to said plate, a second end portion for receiving an implement and a hollow intermediate portion between and spacing said end portions; and
    attaching means for coupling said first end portion of said tube to said base portion, said attaching means including a threaded fastener extending through said tube and said plate;
    whereby an implement can be releasably coupled to the prosthesis by inserting and securing one end of the implement within said second end portion of said tube, and said intermediate portion forms a flexible coupling between said base portion and the implement.

2. An attachment according to claim 1 wherein said attaching means releasably couples said tube to said base portion.

3. An attachment according to claim 1 wherein said plate is fixed to said coupling means.

4. An attachment for a prosthesis, comprising:
    a base plate having first and second opposite ends;
    coupling means, attached to and extending from an extension of said first end of said base plate, for releasably attaching said base plate to a prosthesis;
    a flexible and resilient plastic tube extending axially from said second end and coaxially relative to said coupling means, one end portion of said tube surrounding said plate; and
    attaching means for coupling said tube to said base plate, said attaching means extending through said tube end portion and said plate;
    whereby an implement can be releasably coupled to the prosthesis by inserting and securing one end of the implement within said tube.

5. An attachment according to claim 4 wherein said attaching means comprises a fastener.

6. An attachment according to claim 4 wherein said attaching means comprises a plurality of bolts extending completely through aligned openings in said tube and said plate, and a plurality of nuts threaded on said bolts.

7. An attachment according to claim 1 wherein said tube is straight.

8. A golfing attachment for connecting a golf club to a prosthesis, comprising:
   a base portion having a plate with first and second opposite ends;
   coupling means, attached to and extending from said first end of said plate by an extension, for releasably attaching said base portion to a prosthesis;
   a flexible and resilient plastic tube extending axially from said second end, said tube having a first end portion coupled to and surrounding said plate, a second end portion and a hollow intermediate portion between and spacing said end portions;
   attaching means for coupling said first end portion of said tube to said base portion, said attaching means extending through said tube end portion and said plate; and
   a golf club having a handle portion inserted into and secured to said second end portion of said tube such that said intermediate portion of said tube spaces said handle from said base portion and forms a flexible connection between the prosthesis and said golf club.

9. A golfing attachment according to claim 8 wherein said attaching means releasably couples said tube to said base portion.

10. A golfing attachment according to claim 8 wherein said plate is fixed to said coupling means.

11. A golfing attachment according to claim 8 wherein said attaching means comprises a threaded fastener extending through said tube and said plate.

12. A golfing attachment according to claim 8 wherein said attaching means comprises a fastener.

13. A golfing attachment according to claim 8 wherein said attaching means comprises a plurality of bolts extending completely through aligned openings in said tube and said plate, and a plurality of nuts threaded on said bolts.

14. A golfing attachment according to claim 8 wherein said tube is straight.

15. An attachment according to claim 1 wherein an implement is received in said second end portion of said tube and is spaced from said base portion by said intermediate portion.

* * * * *